(12) United States Patent
Ogle et al.

(10) Patent No.: US 9,606,039 B2
(45) Date of Patent: Mar. 28, 2017

(54) MULTIPHOTON SCANNING FLOW CYTOMETER FOR MULTICELLULAR AGGREGATES

(75) Inventors: Brenda M. Ogle, Fitchburg, WI (US);
Luis A. Fernandez, Madison, WI (US);
Kevin W. Eliceiri, Madison, WI (US);
Matthew S. Hanson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1639 days.

(21) Appl. No.: 12/561,102

(22) Filed: Sep. 16, 2009

(65) Prior Publication Data

US 2011/0065143 A1 Mar. 17, 2011

(51) Int. Cl.
*G01N 33/00* (2006.01)
*B01L 3/00* (2006.01)
*G01N 15/04* (2006.01)

(52) U.S. Cl.
CPC .................................. *G01N 15/04* (2013.01)

(58) Field of Classification Search
CPC .. C12Q 1/68; C12Q 2525/179; C12Q 1/6813;
B01L 3/5027; B01J 2219/00315; B01J
2219/00317; B01J 2219/00707; B01J
2219/00743; G01N 15/1459; G01N
15/1475; G01N 2015/1486; G01N
2015/149; G01N 2015/1497; G01N
21/6428; G01N 21/6452; G01N 21/6458;
G01N 33/5008; G01N 33/5076; G01N
33/582; G01N 15/1468; G01N 33/54366;
G01N 15/04; G01N 2015/1472; G01N
2015/1479; G01N 2015/1488; G01N
2035/00158; G01N 2035/0424; G01N
2510/00; G01N 33/533; G01N 33/566;
G02B 21/32; C12M 23/16; C12M 35/02
USPC ......... 422/73, 500, 501, 502, 503, 504, 505,
422/509, 521, 930
See application file for complete search history.

(56) References Cited

U.S. PATENT DOCUMENTS 6,537,829 B1 * 3/2003 Zarling et al. ................ 436/514
2010/0291584 A1 * 11/2010 Tseng et al. ...................... 435/6

FOREIGN PATENT DOCUMENTS

WO WO 2006/034046 3/2006
WO WO 2007/038346 4/2007

* cited by examiner

*Primary Examiner* — Dean Kwak
(74) *Attorney, Agent, or Firm* — Boyle Fredrickson, S.C.

(57) ABSTRACT

A flow cytometry system suitable for characterizing multicellular aggregates during culture and before implantation combines a low shear flow channel with a multiphoton laser scanning microscope, the latter permitting the characterization of interior and exterior cells in optical isolation from other cells for a representative sampling of fluorescent activity. Imaging capabilities permit sophisticated statistical measurements reflecting individual cell characteristics.

13 Claims, 3 Drawing Sheets

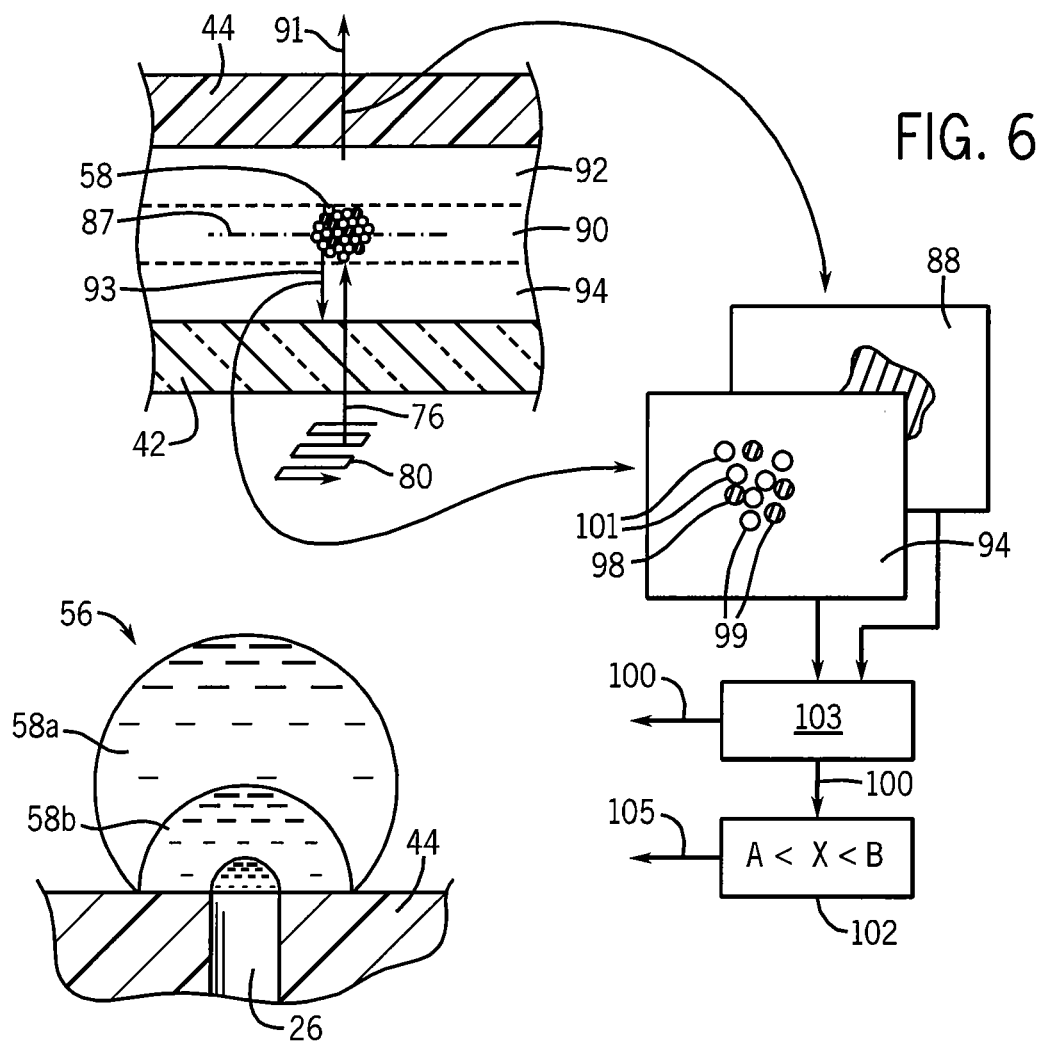
FIG. 6
FIG. 4
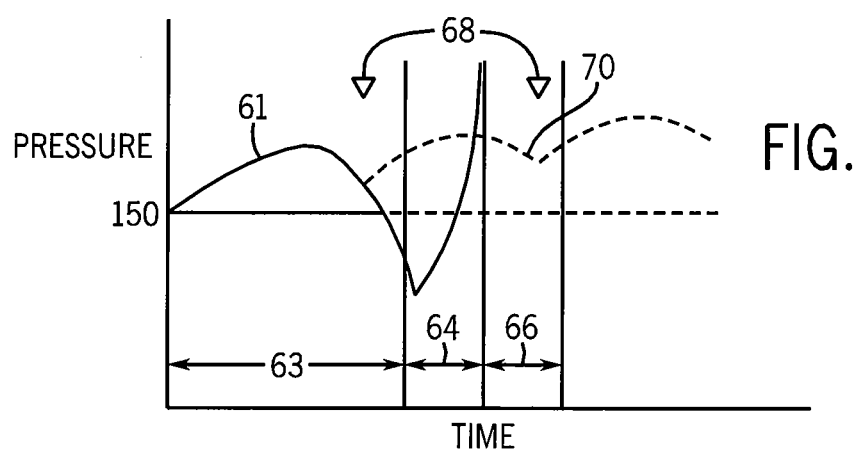
FIG. 5

MULTIPHOTON SCANNING FLOW CYTOMETER FOR MULTICELLULAR AGGREGATES

STATEMENT REGARDING FEDERALLY SPONSORED RESEARCH OR DEVELOPMENT

This invention was made with United States government support awarded by the following agency:
NIH EB000184
The United States government has certain rights in this invention.

CROSS-REFERENCE TO RELATED APPLICATIONS

BACKGROUND OF THE INVENTION

The present invention relates generally to flow cytometers and in particular to a flow cytometer using a multiphoton laser scanning microscope to provide interior fluorescence measurements of multicellular aggregates during flow processing.

The promise of regenerative medicine, using stem or other cells, requires a practical method of assessing multicellular aggregates as they are cultured to determine the viability, proliferative capacity and/or functional competence of the cultured population before implantation. The monitoring system should lend itself to monitoring large numbers of aggregates in an automated or semi automated fashion.

Flow cytometry is a known technique for monitoring individual cells in an automated fashion. In a typical cytometer, individual cells are dispersed in a liquid medium and passed through a channel that hydrodynamically focuses the cells in a line to pass an inspection region. In the inspection region, the cells may be electronically monitored, for example by light absorption, scattering, or fluorescence, and cataloged via high-speed computer. The monitored data may be used to operate a sorting mechanism that may sort the cells according to the monitored data into different channels for separation.

Multicellular aggregates can be disrupted under the sheer forces typically generated in a typical flow cytometer. In addition, conventional flow cytometry monitoring systems are not well adapted for the analysis of three-dimensional cellular structures.

SUMMARY OF THE INVENTION

The present inventors have determined that multicellular aggregates can be processed using flow cytometers with properly designed fluid handling systems that reduce shear forces acting on the multicellular aggregates. In addition, it has been determined that the cells can be sufficiently stabilized at low flow rates to permit analysis of interior structure using a multiphoton laser scanning microscopy. This analysis combines imaging and fluorescence permitting a wide range of characterizations of multicellular aggregates which can be output or used for real time sorting.

Specifically then, the present invention provides a flow cytometry system having a pump communicating with a reservoir to provide a volume flow of liquid from the reservoir to a channel containing the liquid flow. The channel and volume flow are designed to provide a hydrodynamic focusing of multicellular aggregates within the liquid without disruption of intercellular connections of the multicellular aggregate. A multiphoton laser scanning microscope is positioned to illuminate multicellular aggregates within the liquid flow and to record fluorescence of multiple cells of the multicellular aggregates isolated to a focal plane through the multicellular aggregate as the multicellular aggregates reach an analysis point in the channel. A control system, executing at least one stored program, receives data from the multiphoton laser scanning microscope to provide an output signal assessing the multicellular aggregate based on recorded fluorescence from the multiple cells along the focal plane.

It is thus a feature of at least one embodiment of the invention to provide a method of rapidly characterizing interior cells in multicellular aggregates without damage to the inter-cell connections.

The output signal may provide a mapping of fluorescent intensity as a function of two dimensions along the focal plane.

It is thus a feature of at least one embodiment of the invention to combine imaging and fluorescence measurements to provide for more sophisticated analysis metrics.

The output signal may indicate, for example, a proportion of cells exhibiting fluorescence.

It is thus a feature of at least one embodiment of the invention to provide for more sophisticated fluorescence measurements distinguishing fluorescence on a cell-by-cell basis.

The pump may provide a sample stream and a sheath stream combined within the channel so that the sample stream is hydrodynamically focused by the sheath stream and wherein the volumetric flux of the sample stream is 0.1-1 meters per second and a volumetric flux of the sheath stream is 0.5-3.5 meters per second. Alternatively or in addition, sample stream and sheath stream may provide shear forces between cells at the interface between the sheath stream and the sample stream of less than 0.6 mdynes.

It is thus a feature of at least one embodiment of the invention to provide a flow cytometer adapted for analysis of multicellular aggregates.

The pump may be a surface tension pump.

It is thus a feature of at least one embodiment of the invention to provide a simple and intuitive pump system, readily adaptable to the laboratory environment, that can produce controlled flow rates compatible with processing of multicellular aggregates.

The pump may include at least one automated metering pipette applying a series of drops to a channel at a rate and size to provide a surface tension pumping action.

It is thus a feature of at least one embodiment of the invention to provide for accurate control of flow rates of liquids holding multicellular aggregates in a low shear environment.

The pump may use automated metering pipettes to deliver a different series of drops to ports feeding the sheath stream and sample stream to provide different volumetric flow rates in the sheath stream and sample stream. The sheath and sample stream flow rates may be adjusted to provide a flow stream varying in diameter between 300-1600 μm.

It is thus a feature of at least one embodiment of the invention to provide for accurate control of the volumetric ratios, for example, to control the sample stream size for different multicellular aggregates, increasing the versatility of the instrument.

The channel maybe formed of an elastomeric material such as polydimethylsiloxane.

It is thus a feature of at least one embodiment of the invention to provide a high accuracy versatile channel material.

The channel may include a downstream branching, providing alternative paths for the multicellular aggregates, and the flow cytometry system may further including a cell sorter driven by the controller according to the output signal for directing the multicellular aggregates preferentially to a downstream branch.

It is thus a feature of at least one embodiment of the invention to permit sophisticated automated cell sorting.

The cell sorter may use at least one surface tension pump providing a stream intersecting the channel to redirect the multicellular aggregates.

It is thus a feature of at least one embodiment of the invention to provide a sorting mechanism compatible with the goal of preventing damage to the multicellular aggregates.

These particular objects and advantages may apply to only some embodiments falling within the claims, and thus do not define the scope of the invention.

BRIEF DESCRIPTION OF THE FIGURES

FIG. 4 is an expanded cross-sectional view of one droplet of FIG. 3 showing three stages in its evolution with decreasing drop volume;

FIG. 5 is a plot of droplet pressure as a function of time for the three stages of FIG. 4 showing timing of a computer-controlled pipette to refresh the droplet to provide substantially constant pumping pressure;

FIG. 6 is a detailed cross-sectional view of the channel of FIG. 1 showing a suspended multicellular aggregate between sample and shield flows and the acquisition of image and fluorescence data as may be used to develop an output signal characterizing the multicellular aggregate;

DETAILED DESCRIPTION OF THE PREFERRED EMBODIMENT

Figure 1:
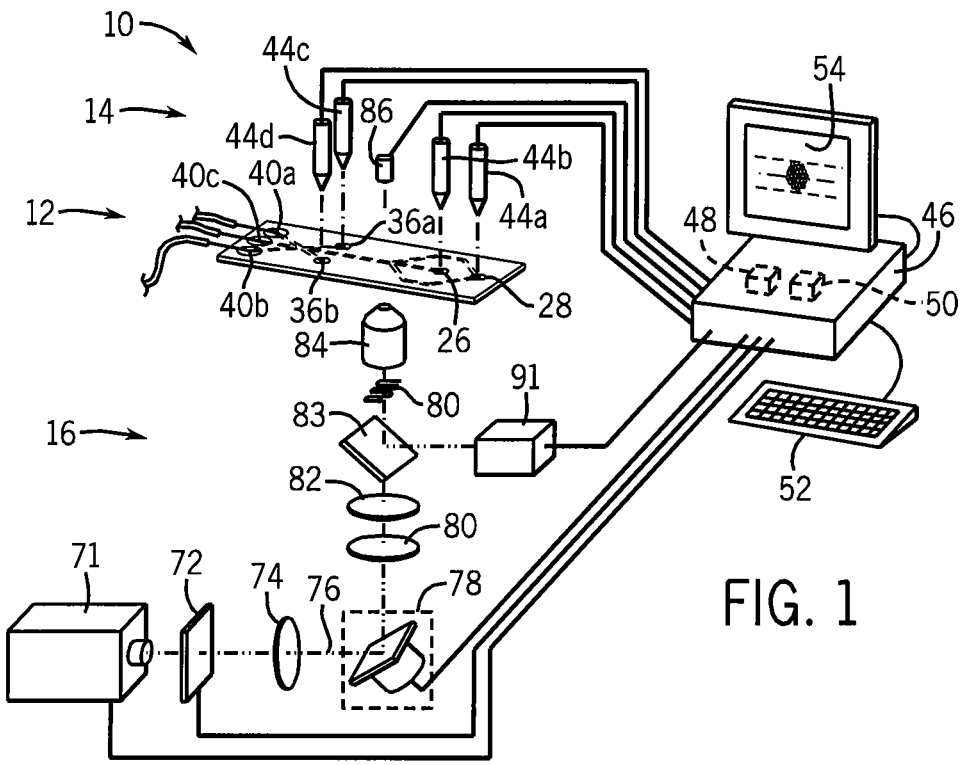
FIG. 1 is an exploded orthogonal view of a flow cytometer according to the present invention showing computer-controlled pipettes providing low shear rate passive pumping in conjunction with a channel assembly positioned for scanning by a multiphoton laser scanning microscope at an inspection point in the channel.

Referring to FIG. 1, a flow cytometer 10 of the present invention generally provides a flow plate 12 receiving liquids from a pump assembly 14 so that liquid flowing through the flow plate 12 may be monitored by a multiphoton laser scanning microscope 16.

Figure 2:
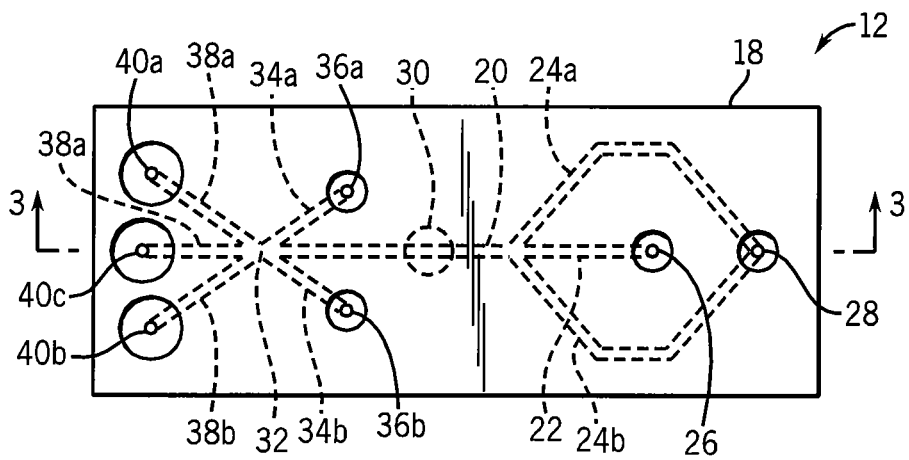
FIG. 2 is a top plan view of the channel assembly used for conducting multicellular aggregates past the inspection point.

Referring to FIG. 2, the flow plate 12 provides a generally horizontal plate 18 holding an analysis channel 20 extending generally along a horizontal axis 21. In one embodiment of the invention, the analysis channel 20 may be 0.7 mm deep (measured along the vertical axis perpendicular to the plane of the plate 18) and 5 mm wide (measured perpendicularly to the axis 21).

An upstream end of the analysis channel 20 communicates with a downstream end of a sample channel 22, axially aligned with the analysis channel 20, and with downstream ends of left and right shield channels 24a and 24b which intersect sample channel 22 at equal and opposed angles. Flow from the shield channels 24a and 24b thus flanks the flow from sample channel 22 to hydrodynamically focus flow from the sample channel 22 into a narrow stream through the analysis channel 20.

The upstream end of the sample channel 22 communicates with a sample port 26 being a vertical bore passing through material forming an upper wall of the sample channel 22 exiting an upper surface of the horizontal plate 18. Similarly, upstream ends of the shield channels 24a and 24b converge on a shield port 28 also being a bore passing upward to the upper surface of the plate 18.

Liquid received through the sample port 26 ultimately is received by the analysis channel 20 to pass an inspection region 30 where it may be inspected by the multiphoton laser scanning microscope 16. The liquid then passes to a sorting junction 32 at a downstream end of the analysis channel 20.

Downstream ends of control channels 34a and 34b communicate with the sorting junction 32 at equal and opposite angles on either side of axis 21. Upstream ends of control channels 34a and 34b terminate at inlet ports 36a and 36b that may receive fluid to provide for corresponding streams in control channels 34a and 34b. These streams from control channels 34a and 34b serve to direct the flow of liquid from the downstream end of analysis channel 20 either leftward or rightward into corresponding sorting channels 38a and 38b respectively.

The sorting channels 38a and 38b diverge at equal angles from the axis 21 on either side of the axis 21. These sorting channels 38a and 38b in turn terminate at upstream ends in a collection port 40a or 40b. A stream of fluid from control channel 34a will thus direct the flow of liquid from the analysis channel 20 into sorting channel 38b and a flow of liquid from control channel 34b will direct the flow from the analysis channel 20 into sorting channel 38a.

When liquid is introduced at neither port 36a nor 36b, the flow from the downstream end of the analysis channel 20 proceeds axially into waste channel 38c to collection port 40c.

Figure 3:
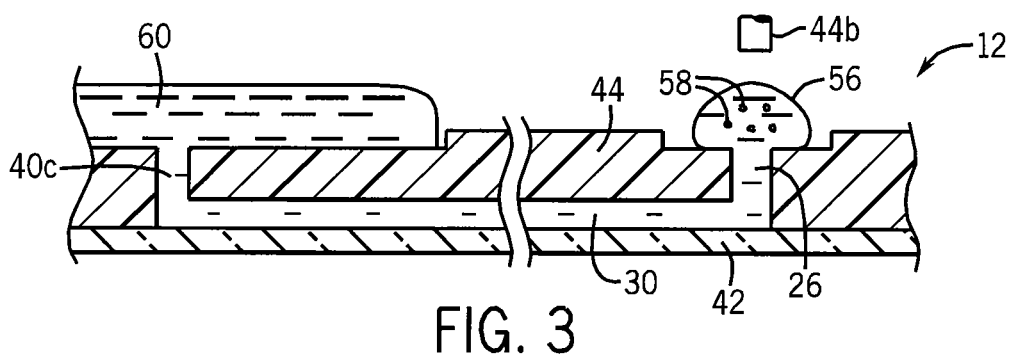
FIG. 3 is a cross-sectional view along line 3-3 of FIG. 2 showing deposited drops providing flow pressure according to the Young-Laplace relationship.

Referring to FIG. 3, the flow plate 12 may be constructed of a lower glass substrate 42 adhered to an upper layer of elastomer 44 incorporating the channels 20, 22, 24, 34, and 38, for example, as molded into the elastomer 44. In one embodiment, the elastomer 44 may be polydimethylsiloxane molded using a template prepared from patterned photoresist on a substrate, the photoresist providing raised portions that form the cores for the channels 20, 22, 24, 34, and 38. In this way, the elastomer 44 may form left, right, and top walls of the channels with the glass substrate 42 forming the bottom walls. The glass substrate 42 may be attached to the elastomer 44 by treating the former with an oxygen plasma. Bores for the ports 26, 28, 36, and 40 may be cut through the elastomer 44 using a sharpened hypodermic needle acting as a tube drill.

Referring again to FIG. 1, liquid may be introduced into the ports 26, 28, and 36 by means of multiple computer-controlled pipettes 44a-44d position above the flow plate 12 to deposit metered drops of liquid on the appropriate ports. Computer-controlled pipettes suitable for this purpose may make use of a nanoliter dispensing valve, for example, the VHS valve commercially available from the Lee Company of Connecticut USA. In this example, computer-controlled pipette 44a may deposit drops over port 28, computer-controlled pipette 44b may deposit drops over port 26, computer-controlled pipette 44c may dispense drops onto port 36a, and computer-controlled pipette 44d may dispense drops onto port 36b.

Computer-controlled pipette 44a will be pre-charged with a shield fluid, for example a saline solution compatible with a multicellular aggregate to be studied. Computer-controlled pipette 44b will be pre-charged with a fluid similar to that of the shield fluid but containing the multicellular aggregates to be analyzed. Computer-controlled pipettes 44c and 44d also will be charged with fluids similar to the shield fluid.

Each of the computer-controlled pipettes 44a-d may be controlled by a central controller 46, for example a computer, providing the necessary electrical interfaces. The central controller 46 will generally include a processor 48, a memory 50 holding a stored program to be described, and a connected conventional user input device 52 and graphics display screen 54 as is generally understood in the art.

Referring now to FIG. 3, the present invention may use surface tension pumping in which a drop 56, for example, is deposited at port 26 by computer-controlled pipette 44b. The surface tension of the liquid of this drop 56 will produce an internal pressure communicating through the port 26 to the sample channel 22 that will move multicellular aggregates 58 into the analysis channel 20. This pressure is resisted by a countervailing pressure, for example by a drop 60 at the waste port 40c, and thus it is the net difference between these pressures that will dictate the flow rate through the analysis channel 20. Generally drop 56 will be on the order of 0.1 to 5 µL and drop 60 one hundred times larger and, as a result, the surface tension pressure generated by drop 56 will be substantially higher than the surface tension pressure generated by drop 60. The large size of drop 60 is further selected so that its surface tension pressure will be substantially constant. The flow rate in the analysis channel 20 will be a function of the density of the fluid, the surface energy of the communicating drops, and the channel resistance.

Referring now also to FIGS. 4 and 5, passive pumping harnesses the higher internal pressure of smaller drops of liquid compared to larger drops of liquid 56 and further takes advantage of a relatively constant region of pressure as drop size shrinks with fluid flow. During a first phase 63 of fluid flow from drop 56 when drop 56 has a peak volume 58a, the internal pressure 61 is substantially constant being bounded by less than a 10% range around an average pressure of 150 Newtons per meter squared. This first phase 63 peaks at droplet contact angles of 90°. At a second phase 64 corresponding generally to smaller peak volume 58b, the pressure varies substantially until the flow ceases at phase 66. The present invention, accordingly, provides a refill droplet from a computer-controlled pipette at times 68 sometime in phase 62 causing the pressure to rebound as indicated by dotted line 70 for substantially continuous pumping pressure with extremely low and accurately controlled pressure ranges suitable for multicellular aggregates. Changing the times 68 can change the average pressure and thus the flow rate provided by the pump.

Generally the refill period may be controlled in an open loop fashion by the controller 46 as will be described below. This passive pumping system provides an extremely simple mechanism that may be readily adapted to a variety of different analysis tasks and compares favorably in accuracy to syringe micro pumps which provide mean pressure values that can change by 5% or more.

Referring to FIG. 6, the multicellular aggregates 58 may be hydrodynamically focused within a stream 90 from the sample channel 22 as flanked by streams 92 from the shield channels 24a and 24b. Although this process is shown in two dimensions, it will be understood that this hydrodynamic focusing may occur in three dimensions to locate the stream 90 and thus the multicellular aggregates 58 in a center of the analysis channel 20 both vertically and horizontally. See generally, "Two simple and rugged designs for creating microfluidic sheath flow" Howell et al, Lab Chip 2008, 8, 1097-1103 thereby incorporated by reference. Generally the size of the stream 90 may be controlled by controlling the relative volume flow rates a being the sum of volumetric flow rates of both shield channels 24a and 24b over the volumetric flow rate of the sample channel 22. In this regard, channel widths varying from 300 µm to 1500 µm (at $\alpha=2$) may be obtained in one embodiment of the invention producing a flow in the outlet channel equal to 600 µL per minute.

Referring again to FIGS. 1 and 2, as multicellular aggregates pass by the inspection region 30, they may be analyzed by the multiphoton laser scanning microscope 16. Such microscopes which are generally known in the art may include a laser 71, for example a Ti:Sapphire laser (for example, as is available from Spectra Physics (Newport Corporation) of Irvine Calif. USA under the tradename Tsunami), providing for wavelength tuning in a range of 700-1100 nm. The beam 76 from the laser 71 may be attenuated by a Pockel's cell 72 (for example, such as commercially available from Conoptics of Danbury Conn.) or similar device controlled by the controller 46 to provide the desired level of illumination of the multicellular aggregates. This beam 76 is then received by a beam expander 74 and a computer-controlled mirror 78 (for example, a galvanometer scanning head such as is commercially available from Cambridge Technologies of Lexington, Mass. USA). The resulting beam 76 may be deflected in a raster pattern by computer-controlled mirror 78 to be received by a scan lens 80 and transfer lens 82. The resulting light is then focused by objective lens 84 (for example, as part of an inverted microscope such as the TE2000 commercially available from Nikon of Japan) on the inspection region 30. Light 91 passing through the inspection region 30 is received by a photodiode 86 whose output is received by the controller 46 to create a coarse bright field image 88 (shown in FIG. 6). Light 93 returned from the multicellular aggregates by two photon or multiphoton induced fluorescence passes back through the objective lens 84 and is received by a dichromatic mirror 83 selecting for the fluorescence frequency which directs the fluorescence to a photomultiplier tube detector 91 (for example, as is commercially available from Hamamatsu of Japan under the tradename 7422) that may comparably make a fluorescence image 94 (shown in FIG. 6) of the multicellular aggregates 58. Generally, the fluorescence image 94 will show fluorescent regions 98 associated with particular cells 99 and non-fluorescent regions 101 that may be distinguished within the resolution of the image 94. In one embodiment, the objective lens 84 may be maintained at a fixed focal distance so that the data is collected on a single focal plane 87 (shown in FIG. 6). A scan speed of approximately 2.33 frames per second with a resolution of 256×256 pixels may be obtained by this system. Scanning speed increases are possible through reduced data acquisition resolution, line scanning approaches and higher-speed acoustic opticalcomputer-controlled mirrors. Accordingly a given multicellular aggregate may be scanned multiple times while in the inspection region 30 and these images averaged for improved image quality.

Referring again to FIG. 6, the combination of fluorescence data (intensity) and image data (a mapping of direct fluorescence or reflected fluorescence along two dimensions of the focal plane 87) may be combined to provide for sophisticated analysis of the multicellular aggregates 58. In a simple example, the fluorescence may be integrated over the fluorescence image 94 and divided by the total area of the image taken from the fluorescence image 94 or the bright field image 88. This provides a measure of the proportion of cells providing fluorescence such as may indicate a certain metabolic activity (for inherent fluorescence) or uptake of exogenous florophores providing information about the phenotype of the cell, the ability of the cell to function or the interaction of the cell with its microenvironment. More sophisticated image processing of the fluorescence image 94 can provide for a cell count in the image and can associate individual cells with peaks of fluorescent activity to also provide a proportion of the cells within the sample exhibiting fluorescence. Note that the operation of the multiphoton laser scanning microscope 16 is such as to reject the measurement of cells outside of the focal plane 87 with a high rejection rate caused by the precise focus of the multiple photons necessary for multiphoton fluorescence on the focal plane 87.

The fluorescence image 94 and/or bright field image 88 may be output to the display screen 54 (shown in FIG. 1) as well as a quantitative measurement 100 extracted by an image processing engine 103, for example, providing morphometric filters providing the analysis described above with respect to indicating a proportion of cellular fluorescence. The quantitative measurement 100 may also be received by a range comparator 102 that may be used for sorting purposes to sort cells according to whether they are above or below pre-established ranges (A or B) and provide a sorting signal 105 that may operate a cell sorting device.

Referring again to FIG. 1, the sorting signal 105 (shown in FIG. 6) may be used to activate computer-controlled pipettes 44c or 44d for sorting of cells when they reach the sorting junction 32 (shown in FIG. 2).

Figure 7:
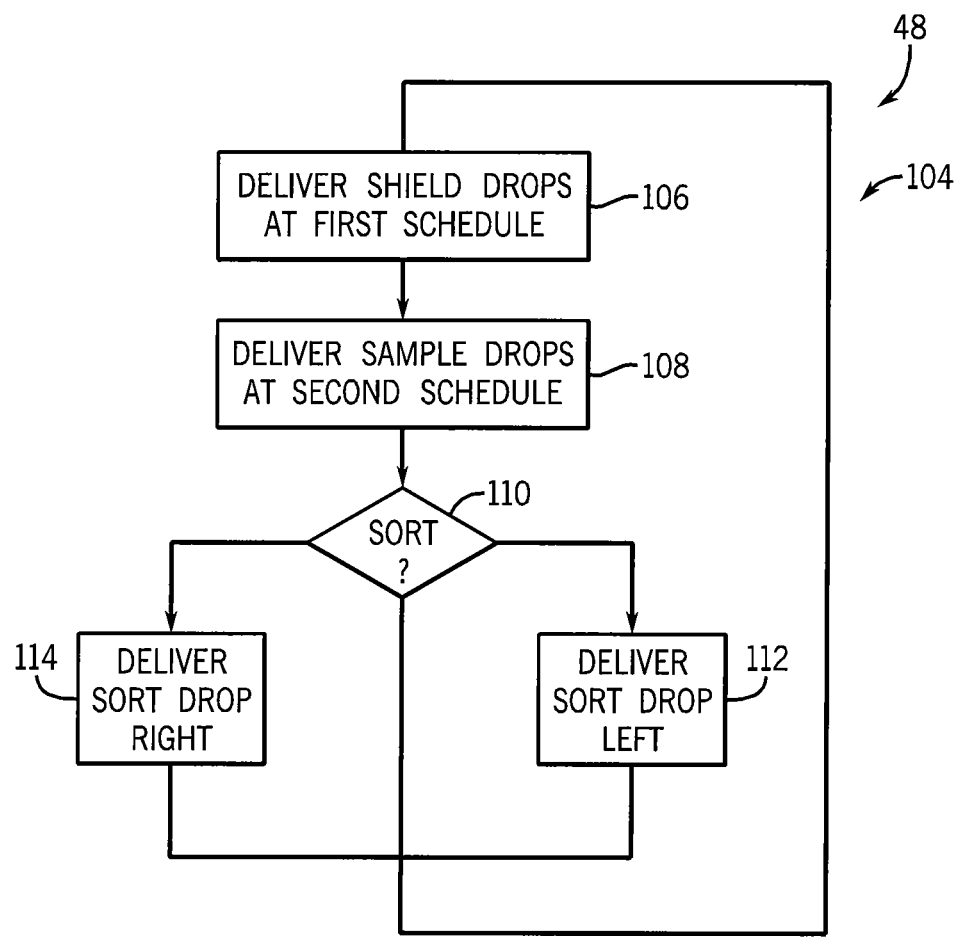
FIG. 7 is a flow chart of a program executed by the computer of FIG. 1 to control the computer-controlled pipettes.

Referring now to FIG. 7, in this regard the controller 46 executing the stored program 104 in memory 50 may at a first process block 106 check a shield fluid delivery schedule and activate computer-controlled pipette 44a if a drop is scheduled to be delivered to port 28. Similarly at succeeding process block 108, a sample fluid delivery schedule is checked and computer-controlled pipette 44b activated if a drop is scheduled to be delivered to port 26. At decision block 110, the sorting signal 105 is evaluated to see if a sorting should occur. If so, at process block 112 or process block 114, depending on which of the ranges A or B has been crossed, after a suitable transport delay time between inspection region 30 and sorting junction 32, one of computer-controlled pipettes 44d or 44c is activated as appropriate. Again, this surface tension pumping provides for flow rates consistent with the preservation of the integrity of the multicellular aggregates 58.

The present invention may be used for the evaluation of embryonic bodies or pancreatic islets and many other forms of multicellular aggregates. The data collected may be used to analyze these multicellular aggregates not simply with respect to the spatial distribution of fluorescence within the cells or the phenotypes of the cells or other techniques described above, but also with respect to the spectra of the fluorescence and fluorescence lifetime in order to get a read out of chemical interaction between the cells and the microenvironment. Spectra can be obtained by modification of the photomultiplier measuring fluorescence to provide for spectrographic capabilities, for example, by appropriate optics. The analysis of the intrinsic fluorescence may allow a metabolic profiling of stem cell differentiation on the basis of NADH and FAD signals.

It is specifically intended that the present invention not be limited to the embodiments and illustrations contained herein, but include modified forms of those embodiments including portions of the embodiments and combinations of elements of different embodiments as come within the scope of the following claims.

We claim:

1. A flow cytometry system comprising:
   a pump providing an unconfined volume of liquid subject to an applied force;
   a channel receiving a liquid flow from the pump, the channel containing the liquid flow along an axis providing a hydrodynamic focusing of a multicellular aggregate within the liquid without disruption of intercellular connections of the multicellular aggregate;
   a multiphoton laser scanning microscope positioned to illuminate multicellular aggregates within the liquid flow and to record a fluorescence of multiple cells of the multicellular aggregates isolated to a focal plane through the multicellular aggregates as the multicellular aggregates reach an analysis point in the channel; and
   a control system executing at least one stored program to receive data from the multiphoton laser scanning microscope to provide an output signal providing an assessment of the multicellular aggregates based on recorded fluorescence from the multiple cells along the focal plane.

2. The flow cytometry system of claim 1 wherein the output signal is adapted to provide a mapping of fluorescent intensity as a function of two dimensions along the focal plane.

3. The flow cytometry system of claim 1 wherein the output signal is adapted to indicate a proportion of cells exhibiting fluorescence.

4. The flow cytometry system of claim 1 wherein the pump is adapted to provide a sample stream and a sheath stream combined within the channel so that the sample stream is hydrodynamically focused by the sheath stream and wherein a volumetric flux of the sample stream is 0.1-1 meters per second and a volumetric flux of the sheath stream is 0.5-3.5 meters per second.

5. The flow cytometry system of claim 1 wherein the pump is adapted to provide a sample stream and a sheath stream combined within the channel so that the sample stream is hydrodynamically focused by the sheath stream and wherein a shear force between cells at an interface between the sheath stream and the sample stream is less than 0.6 mdynes.

6. The flow cytometry system of claim 1 wherein the pump is a surface tension pump.

7. The flow cytometry system of claim 6 wherein the pump includes at least one automated metering pipette applying a series of drops to a channel in a size that provides a surface tension pumping action.

8. The flow cytometry system of claim 7 wherein the pump provides a sample stream and a sheath stream combined within the channel so that the sample stream is hydrodynamically focused by the sheath stream and wherein the control system further provides signals to first and second automated metering pipettes so that a different series of drops to ports feeding the sheath stream and sample stream provide different volumetric flow rates in the sheath stream and sample stream.

9. The flow cytometry system of claim 8 wherein the control system provides different volumetric flow rates to control the flow stream within the channel to a range of diameters of 300-1600 μm in diameter.

10. The flow cytometry system of claim 1 wherein the channel is formed of an elastomeric material.

11. The flow cytometry system of claim 10 wherein the channel is molded polydimethylsiloxane.

12. The flow cytometry system of claim 1 wherein the channel is further adapted to include a downstream branching providing alternative paths for the multicellular aggregates and further including a cell sorter driven by the control system according to the output signal for directing the multicellular aggregates preferentially to a downstream branch.

13. The flow cytometry system of claim 12 wherein the cell sorter consists of at least one surface tension pump providing a stream intersecting the channel to redirect the multicellular aggregates.

* * * * *